(12) United States Patent
Pafford et al.

(10) Patent No.: US 7,906,671 B2
(45) Date of Patent: Mar. 15, 2011

(54) FLUIDS HAVING SILICONE GROUPS AND ORGANIC GROUPS CONTAINING ESTERS

(75) Inventors: Bernie John Pafford, Berkeley Heights, NJ (US); Wenning Wang Han, Lawrenceville, NJ (US); Suzzy Chen Hsi Ho, Princeton, NJ (US); Nicole Blandine Temme, Rahway, NJ (US); James Zielinski, Somerset, NJ (US); Anthony J. O'Lenick, Jr., Dacula, GA (US); Rick Vrckovnik, Toronto (CA); Mark W. Riddle, Toronto (CA)

(73) Assignees: ExxonMobil Chemical Patents Inc., Houston, TX (US); Siltech Corporation (CA)

( * ) Notice: Subject to any disclaimer, the term of this patent is extended or adjusted under 35 U.S.C. 154(b) by 1167 days.

(21) Appl. No.: 11/556,234

(22) Filed: Nov. 3, 2006

(65) Prior Publication Data

US 2008/0108842 A1    May 8, 2008

(51) Int. Cl.
*C07F 7/08* (2006.01)
(52) U.S. Cl. ...................................................... 556/439
(58) Field of Classification Search ................... 556/439
See application file for complete search history.

(56) References Cited

U.S. PATENT DOCUMENTS

| | | |
|---|---|---|
| 4,257,936 A | 3/1981 | Matsumoto et al. |
| 4,287,109 A | 9/1981 | Schlak et al. |
| 4,472,565 A | 9/1984 | Ryang |
| 4,588,770 A | 5/1986 | Wuerminghausen et al. |
| 4,780,510 A | 10/1988 | Uemiya et al. |
| 5,472,686 A | 12/1995 | Tsubaki et al. |
| 5,561,231 A | 10/1996 | Dauth et al. |
| 5,660,819 A | 8/1997 | Tsubaki et al. |
| 5,698,502 A | 12/1997 | Pafford et al. |
| 5,741,552 A | 4/1998 | Takayama et al. |
| 5,808,127 A | 9/1998 | Nakagawa et al. |
| 6,004,540 A | 12/1999 | Richard et al. |
| 6,158,995 A | 12/2000 | Muramatsu et al. |
| 6,177,387 B1 | 1/2001 | Schlosberg et al. |
| 6,257,846 B1 | 7/2001 | Muramatsu et al. |
| 6,274,688 B1 | 8/2001 | Nakagawa et al. |
| 6,423,787 B1 | 7/2002 | Kitano et al. |
| 6,660,399 B1 | 12/2003 | Kitano et al. |
| 6,790,451 B2 | 9/2004 | Nakanishi |
| 6,794,461 B2 | 9/2004 | Fujita et al. |
| 6,844,301 B2 | 1/2005 | Field et al. |

*Primary Examiner* — Elvis O Price
(74) *Attorney, Agent, or Firm* — Ohlandt, Greeley, Ruggiero & Perle, LLP

(57) ABSTRACT

A silicone composition having the formula:

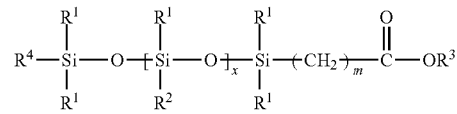

wherein $R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing and a reverse ester thereof; provided that if $R^1$ is anything but methyl or ethyl, then $R^2$ must be a methyl, ethyl or butyl.

27 Claims, 5 Drawing Sheets

FLUIDS HAVING SILICONE GROUPS AND ORGANIC GROUPS CONTAINING ESTERS

BACKGROUND

1. Technical Field

The present disclosure relates to silicone based fluids having silicon groups and organic groups linked through ester linkages. More particularly, the present disclosure relates to silicone based fluids that are formed from the reaction of vinyl-terminated carboxylic acid esters of partially esterified esters with hydride containing polysiloxanes. The vinyl-terminated carboxylic acid esters of partially esterified esters are formed from the reaction of multifunctional alcohols with vinyl-terminated carboxylic acids.

2. Description of the Related Art

The utility of polyol ester compositions with unconverted hydroxyl groups as lubricant base stocks has been described in U.S. Pat. No. 5,698,502.

Silicone compounds have a number of positive attributes, including excellent thermal stability. However, the problem of limited solubility in a variety of hydrocarbons reduces the potential applications.

Siltech has pioneered the functionalization of hydrocarbons onto silicone compounds, but typically these hydrocarbons have been linear structures. The ability to functionalize a branched hydrocarbon onto silicone compounds could lead to products with different solubilities, thermal stabilities, and other properties that can move beyond current materials. Accordingly, the present disclosure provides silicone compounds having functionalized branched hydrocarbon groups.

SUMMARY

Disclosed herein is a silicone composition having the formula:

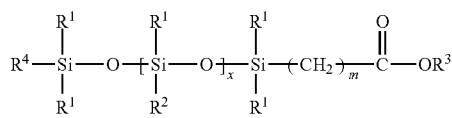

wherein:

$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, an ester-containing group represented by the formula:

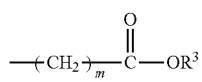

and a reverse ester thereof represented by the formula:

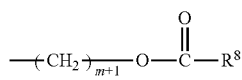

and the formula:

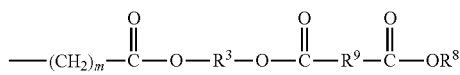

and a reverse ester thereof represented by the formula:

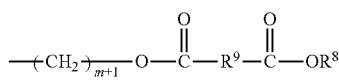

provided that if $R^1$ is anything but methyl or ethyl, then $R^2$ must be a methyl, ethyl or butyl, $R^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)5CH3<br>\|<br>H5C2—C---CH2OH<br>\|<br>CH2OOC(CH2)5CH3 | CH2OOC(CH2)5CH3<br>\|<br>H5C2—C—CH2----<br>\|<br>CH2OOC(CH2)5CH3 |

Where in this case the two esterified groups on the molecule have been reacted with heptanoic acid.

$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;

$R^9$ is selected from the group consisting of: an arylene, an alkylene of 1 to 22 carbon atoms, substituted alkylene of 1 to 22 carbon atoms optionally substituted by one or more fluorine atoms and arylene;

$R^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof;

m is an integer between about 5 to about 22; and x is an integer between about 0 to about 1000;

wherein said composition has at least 1 compound derived from said partially esterified ester-containing group or and said reverse ester thereof.

Preferably, $R^1$ and $R^2$ are both methyl groups and m is an integer between about 10 to about 14, preferably m is 10. Moreover, x is an integer in the range between about 6 to about 110, preferably between about 6 to about 50.

The compound derived from said partially esterified ester residue is a partially esterified alcohol. The mono-hydroxy-terminated partially esterified alcohol is derived from a polyfunctional alcohol represented by the formula:

$R^5(OH)_n$ wherein:

$R^5$ is an n-functional hydrocarbon; and n is from about 2 to about 8, preferably between about 2 to about 4.

The functional alcohol is preferably selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof. The preferred functional alcohol is trimethylolpropane.

The compound derived from said partially esterified ester residue is a partially esterified acid. The mono-hydroxy-terminated partially esterified acid is derived from multi-functional acids. The functional acid can be selected from the group consisting of any C2 to C12 diacids, e.g., adipic, azelaic, sebacic, and dodecanedioc, succinic acid, glutaric acid, maleic acid, phthalic acid, trimellitic acid, nadic acid, methyl nadic acid, hexahydrophthalic acid and mixtures thereof.

Anhydrides of polybasic acids can be used in place of the multifunctional acids. The functional anhydride is selected from the group consisting of: succinic anhydride, glutaric anhydride, adipic anhydride, maleic anhydride, phthalic anhydride, trimellitic anhydride, nadic anhydride, methyl nadic anhydride, hexahydrophthalic anhydride, and mixtures thereof.

$R^4$ is preferably a group represented by the formula:

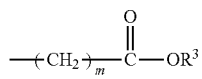

wherein:
$R^3$ is a compound derived from a partially esterified ester residue;
m is an integer in the range between about 5 to about 22; and
x is an integer in the range between about 0 to about 1000, or a reverse ester thereof represented by the formula:

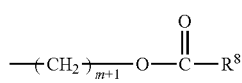

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue.

Alternatively, $R^4$ is a methyl group.

The silicone composition represented by the formula:

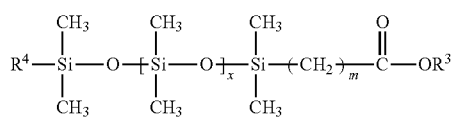

wherein:
$R^4$ is selected from the group consisting of methyl and a group represented by the formula:

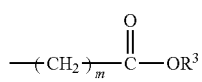

$R^3$ is a compound derived from a partial ester residue;
m is 10; and x is an integer in the range between about 0 to about 1000, preferably about 6 to about 110.

$R^4$ is preferably a group represented by the formula:

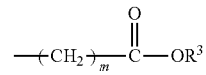

wherein $R^3$ is a compound derived from a partially esterified ester residue. The partially esterified ester residue is derived from a mono-hydroxy-terminated partially esterified alcohol. The mono-hydroxy-terminated partially esterified alcohol is derived from di-, tri- or tetra-functional alcohol represented by the formula:

$R^5(OH)_n$ wherein:
$R^5$ is an n-functional hydrocarbon residue; and
n is an integer in the range between about 2 to about 8, preferably between about 2 to about 4.

Preferably, the di-, tri- or tetra-functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

Preferably, the functional alcohol is trimethylolpropane and $R^4$ is a group represented by the formula:

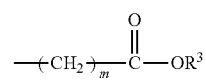

wherein:
$R^3$ is a compound derived from a partially esterified ester residue;
m is an integer in the range between about 5 to about 22; and
x is an integer in the range between about 0 to about 1000, or a reverse ester thereof represented by the formula:

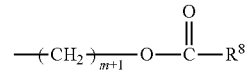

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue. Alternatively, $R^4$ is a methyl group.

The partially esterified ester is represented by the formula:

$(R^7COO)_{n-1}R^6(OH)$ wherein:
$R^6$ is an (n-1)-functional hydrocarbon residue group;
$R^7$ is a hydrocarbyl group; and
n is an integer in the range between about 2 to about 8.

According to another embodiment of the present disclosure, a silicone composition is represented by the formula:

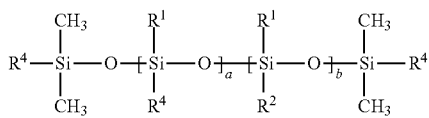

wherein $R^4$ is selected from the group consisting of: alkyl and a group represented by the formula:

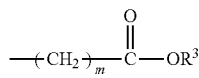

wherein:
a is an integer in the range between about 1 to about 20;
b is an integer in the range between about 0 to about 1000;
$R^3$ is a compound derived from a partially esterified ester residue; and
m is an integer in the range between about 5 to about 22;
with the proviso that the $R^4$ groups are not all alkyls.

A process for preparing a silicone composition comprising: contacting
(i) an hydride terminated polysiloxane represented by the formula:

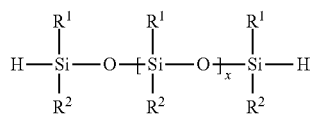

and
(ii) a vinyl-terminated partially esterified ester-containing compound represented by the formula:

$$CH_2=CH-(CH_2)_{m-2}-COOR$$

or a reverse ester thereof;
at a temperature and for a period of time sufficient to produce a silicone composition represented by the formula:

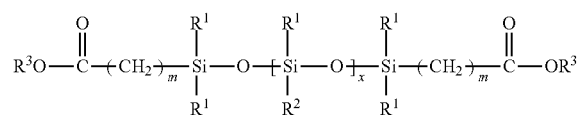

or a reverse ester thereof; wherein:
$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, and aryl;
$R^3$ is a compound derived from a partially esterified ester-containing group;
m is an integer in the range between about 5 to about 22, preferably between about 10 to about 14, most preferably 10; and x is an integer in the range between about 0 to about 1000, preferably between about 6 to about 110, most preferably between about 6 to about 50.
Preferably, $R^1$ and $R^2$ are both methyl groups.
The compound derived from said partially esterified ester residue is a mono-hydroxy-terminated partially esterified alcohol. The mono-hydroxy-terminated partially esterified alcohol is derived from di-, tri- or tetra-functional alcohol represented by the formula:

$$R^5(OH)_n$$

wherein:
$R^5$ is an n-functional hydrocarbon residue; and
n is an integer in the range between about 2 to about 8, preferably between about 2 to about 4.
The functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof, preferably trimethylolpropane.
The mono-hydroxy-terminated partially esterified ester is represented by the formula:

$$(R^7COO)_{n-1}R^6(OH)$$

wherein:
$R^6$ is an (n-1)-functional hydrocarbon residue;
$R^7$ is a hydrocarbyl group; and
n is an integer in the range between about 2 to about 8.
The vinyl-terminated carboxylic acid ester of a partially esterified ester is represented by the formula:

$$CH_2=CH-(CH_2)_{m-2}-COOR^6(OOCR^7)_{n-1}$$

wherein:
$R^6$ is an (n-1)-functional hydrocarbon residue;
$R^7$ is a hydrocarbyl group;
m is an integer in the range between about 5 to about 22; and
n is an integer in the range between about 2 to about 8.
The vinyl-terminated carboxylic acid ester of a partially esterified ester is formed by reacting a partially esterified ester with either an olefinic acid, methyl ester or anhydride.
The present disclosure also includes a process for preparing a silicone composition comprising:
reacting a partially esterified ester with either an olefinic acid or alcohol, thereby producing a vinyl-terminated carboxylic acid ester of a partially esterified ester; and hydrosilating said vinyl-terminated carboxylic acid ester of partially esterified ester.
Preferably, the vinyl-terminated carboxylic acid ester of a partially esterified ester is hydrosilated with a hydride terminated polysiloxane represented by the following formula:

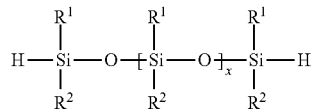

wherein:
$R^1$ and $R^2$ are independently selected from the group consisting of: methyl, ethyl and phenyl; and
x is an integer in the range between about 0 to about 1000.
The vinyl-terminated carboxylic acid ester of a partially esterified ester is represented by the formula:

$$CH_2=CH-(CH_2)_{m-2}-COOR^3$$

$R^3$ is a compound derived from a partially esterified ester residue; and m is an integer in the range between about 5 to about 22.

The silicone compound preferably has the formula:

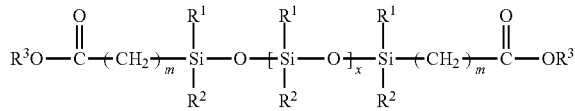

wherein:

$R^1$ and $R^2$ are independently selected from the group consisting of: methyl, ethyl and phenyl;

$R^3$ is a compound derived from a partially esterified ester residue;

m is an integer in the range between about 5 to about 22; and x is an integer in the range between about 0 to about 1000.

The present disclosure also includes a process for preparing a silicone composition comprising: reacting a partial ester with a silicone compound, wherein said silicone compound is the reaction product comprising the reaction of silicone with either an olefinic acid or alcohol. The silicone compound is a hydride terminated polysiloxane represented by the formula:

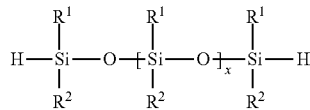

wherein:

$R^1$ and $R^2$ are independently selected from the group consisting of: methyl, ethyl and phenyl; and x is an integer in the range between about 0 to about 1000.

DETAILED DESCRIPTION OF THE PREFERRED EMBODIMENTS

Figure 1:
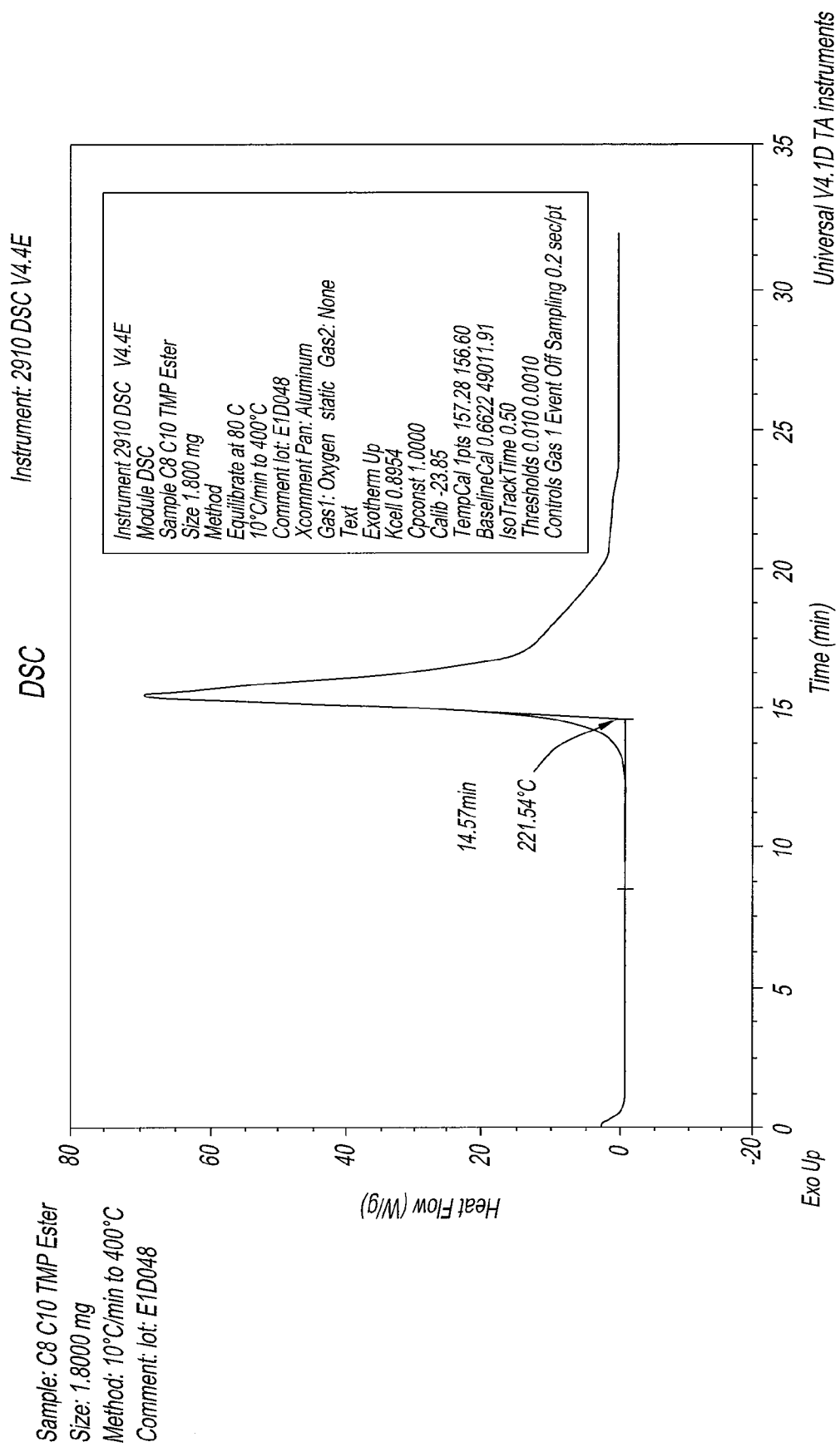
FIG. 1 shows the Pressure Differential Scanning Calorimetry (PDSC) Spectrum of a fully esterified ester of trimethylol propane with linear octanoic and decanoic acids.

In a preferred embodiment, $R^1$ and $R^2$ are independently selected from hydrogen, alkyl of 1 to 45 carbon atoms, substituted alkyl of 1 to 45 carbon atoms optionally substituted by one or more fluorine atoms and aryl. More preferably, $R^1$ and $R^2$ are both methyl groups.

Preferably, m is from about 10 to about 14, most preferably m is 10.

Preferably, x is from about 6 to about 110, most preferably x is from about 6 to about 50.

$R^3$ is preferably a mono-hydroxy-terminated partially esterified ester.

The mono-hydroxy-terminated partially esterified ester residue is derived from a mono-hydroxy-terminated partially esterified alcohol. That is, the mono-hydroxy-terminated partially esterified alcohol is derived from di-, tri- or tetra-functional alcohol represented by the formula:

wherein:

$R^5$ is an n-functional hydrocarbon residue; and n is from about 2 to about 8, preferably from 2 to 4.

The functional alcohol is preferably selected from ethylene glycol, propylene glycol, butylene glycol, polyethylene glycol, neopentyl glycol polypropylene glycol, glycerin, trimethylolethane, trimethylolpropane, pentaerythritol, di-pentaerythritol, tri-pentaerythritol, and a mixture there, most preferably the functional alcohol is trimethylolpropane.

$R^4$ is a group represented by the formula:

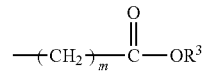

wherein:

$R^3$ is a compound derived from a partially esterified ester residue;

m is an integer in the range between about 5 to about 22; and x is an integer in the range between about 0 to about 1000, or a reverse ester thereof represented by the formula:

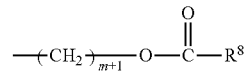

wherein $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue. Alternatively, $R^4$ is a methyl group.

The silicone composition represented by the formula:

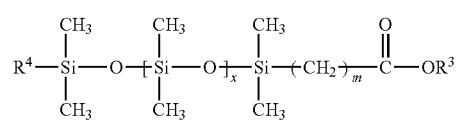

wherein:

$R^4$ is selected from the group consisting of methyl and a group represented by the formula:

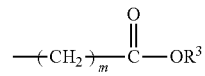

$R^3$ is a monohydroxy-terminated partial ester residue;

m is 10; and x is from about 6 to about 110, preferably from about 6 to about 50.

R$^4$ can be a group represented by the formula:

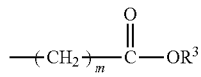

wherein R$^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)$_5$CH3<br>\|<br>H5C2—C- - -CH2OH<br>\|<br>CH2OOC(CH2)$_5$CH3 | CH2OOC(CH2)$_5$CH3<br>\|<br>H5C2—C—CH2- - - -<br>\|<br>CH2OOC(CH2)$_5$CH3 |

Where in this case the two esterified groups on the molecule have been reacted with heptanoic acid.

The mono-hydroxy-terminated partially esterified ester residue is derived from a mono-hydroxy-terminated partially esterified alcohol.

Preferably, the mono-hydroxy-terminated partially esterified alcohol is derived from di-, tri- or tetra-functional alcohol represented by the formula:

R$^5$(OH)$_n$ wherein:
R$^5$ is an n-functional hydrocarbon residue; and
n is from about 2 to about 8, preferably from 2 to 4.

Preferably, the di-, tri- or tetra-functional alcohol is selected from ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof, most preferably trimethylolpropane.

Alternatively, the mono-hydroxy-terminated partially esterified ester is represented by the formula:

(R$^7$COO)$_{n-1}$R$^6$(OH)

wherein:
R$^6$ is an (n-1)-functional hydrocarbon residue group;
R$^7$ is a hydrocarbyl group; and
n is from about 2 to about 4.

Preferably, the vinyl-terminated carboxylic acid ester of a partially esterified ester is represented by the formula:

CH$_2$=CH—(CH$_2$)$_{m-2}$—COOR$^6$(OOCR$^7$)$_{n-1}$ wherein:
R$^6$ is an (n-1)-functional hydrocarbon residue;
R$^7$ is a hydrocarbyl group;
m is about 5 to about 22; and
n is from about 2 to about 8, preferably from about 2 to about 4.

Preferably, the vinyl-terminated carboxylic acid ester of a partially esterified ester is formed by reacting a mono-hydroxy-terminated partially esterified ester with either an olefinic acid, methyl ester or anhydride.

Preferably, the vinyl-terminated carboxylic acid ester of a partially esterified ester is hydrosilated with a hydride terminated polysiloxane represented by the formula:

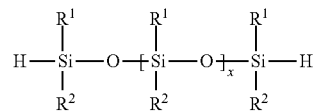

wherein:
R$^1$ and R$^2$ are independently selected from methyl, ethyl and phenyl; and
x is from about 0 to about 1000.

Alternatively, the hydride can be located internally.

Preferably, the vinyl-terminated carboxylic acid ester of a partially esterified ester is represented by the following formula:

CH$_2$=CH—(CH$_2$)$_{m-2}$—COOR$^3$

R$^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)$_5$CH3<br>\|<br>H5C2—C- - -CH2OH<br>\|<br>CH2OOC(CH2)$_5$CH3 | CH2OOC(CH2)$_5$CH3<br>\|<br>H5C2—C—CH2- - - -<br>\|<br>CH2OOC(CH2)$_5$CH3 | where in this case the two esterified groups on the molecule have been reacted with heptanoic acid; and
m is from about 5 to about 22.

The silicone ester compound formed according to the preferred method has the formula:

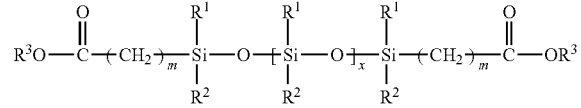

wherein:
R$^1$ and R$^2$ are independently selected from methyl, ethyl and phenyl;
R$^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)$_5$CH3<br>\|<br>H5C2—C- - -CH2OH<br>\|<br>CH2OOC(CH2)$_5$CH3 | CH2OOC(CH2)$_5$CH3<br>\|<br>H5C2—C—CH2- - - -<br>\|<br>CH2OOC(CH2)$_5$CH3 | where in this case the two esterified groups on the molecule have been reacted with heptanoic acid;
m is from about 5 to about 22; and
x is from about 0 to about 1000.

Preferably, the silicone hydride precursor is represented by the formula:

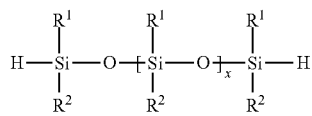

wherein:
$R^1$ and $R^2$ are independently selected from methyl, ethyl and phenyl; and
x is from about 0 to about 1000.
Alternatively, the hydride can be located internally.

In a preferred embodiment, the silicone hydride precursor has one or more block polymers or block copolymers in the backbone. For example, the backbone group represented by the formula:

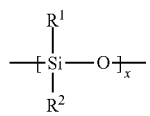

can have one or more of the same or different block copolymers and the silicone ester compound can be represented by the formula:

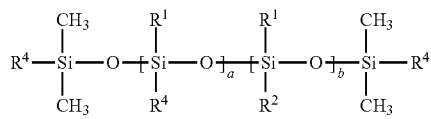

wherein $R^4$ is selected from alkyl and a group represented by the formula:

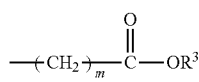

a is an integer from 1 to 20;
b is an integer from 0 to 200;
$R^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)5CH3<br>\|<br>H5C2—C---CH2OH<br>\|<br>CH2OOC(CH2)5CH3 | CH2OOC(CH2)5CH3<br>\|<br>H5C2—C—CH2----<br>\|<br>CH2OOC(CH2)5CH3 | where in this case the two esterified groups on the molecule have been reacted with heptanoic acid; and
m is an integer from about 5 to about 22; with the proviso that all $R^4$ groups are not alkyl.

The hydride terminated polysiloxane and vinyl terminated carboxylic ester of a partially esterified ester are heated to 80-120° C. and a platinum hydrosilation catalyst such as chloroplatinic acid or any other platinum catalyst familiar to those skilled in the art is added up to about 100 ppm. Optionally a solvent such as toluene, xylene, IPA or any other solvent that is familiar to those skilled in the art can be used. The reaction is heated at 80-120° C. until all silicone hydride is consumed, which usually takes about 2-8 hours. If a solvent is used, it is then stripped under vacuum.

Esters have been used for a number of years for a variety of applications including lubricants. In most cases, the esters are fully esterified. For esters of polyhydric alcohols, nearly all the hydroxyl groups have been reacted with acids so that the hydroxyl number is generally less than about 5 (←5).

By limiting the extent of the reaction, for example, by shortening the reaction time or starving the reaction mixture of at least one of the reactants, partial esters can be created. Polyol ester compositions having unconverted hydroxyl groups have been used as lubricant base stocks. Their preparation and uses have been described in U.S. Pat. No. 5,698,502.

Partially reacted esters provide the desired reactive intermediate functional groups for hydrosilation and branching. For example, certain polyhydric alcohols, such as, pentaerythritol, provide a neopentyl carbon with a $CH_2OH$ group attached. Reacting an acid to one, two, or three of these functional groups provides the partial ester.

Partially esterified esters having only one free hydroxyl group are preferred, preferably about 0.7 hydroxyl groups. This reduces opportunities for cross-linking during the hydrosilation process. An example of a preferred hydrosilation process is set forth in U.S. Pat. No. 5,561,231, which is incorporated herein by reference in its entirety.

Other multifunctional alcohols include trimethylolpropane, pentaerythritols, neopentyl glycol, sorbitol and mixtures thereof.

In the practice of the invention, the alcohols are allowed to react with carboxylic acids to produce partially or fully esterified esters or mixtures of partially and fully esterified esters. The acid can be a monocarboxylic acid, such as, octanoic acid, and can vary in chain length to provide the desired branching in the final product. The acid can also be a multifunctional acid. Examples of such multi-functional acids include adipic acid.

Silicone ester compounds with a range of molecular weights can be prepared by reacting the ester created from esterification of a vinyl containing molecule with an esterified ester with a silicone backbone. The resulting compounds have unique properties that make them useful in a number of applications.

The present disclosure further contemplates the use of more complex esters, such as, complex esters resulting from the reaction of polyhydric alcohol with a multifunctional acid followed by further reaction with a monofunctional alcohol to produce a partially esterified ester.

The partially esterified esters can be reacted with an olefinic acid, such as, undecylenic acid and thereafter hydrosilated, for example, with a hydride terminated polysiloxane.

The number of Si atoms in the above molecule represents a preferred range. However, the number of Si atoms could be higher, by way of examples only, as high as a 1000.

Monohydroxy-terminated partial ester can be represented by the formula:

$R^3$—OH wherein R³ is derived from a partially esterified ester residue, e.g., for a partially esterified trimetholpropane shown here, the residue is the structure without the remaining free hydroxyl group

| Partial Ester | Residue |
|---|---|
| 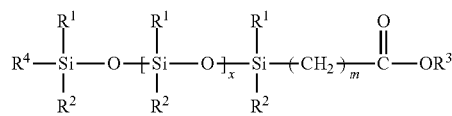 | | where in this case the two esterified groups on the molecule have been reacted with heptanoic acid.

Thus, the present disclosure provides a silicone ester compound with esterified groups represented by the formula:

$$R^4-\underset{\underset{R^2}{|}}{\overset{\overset{R^1}{|}}{Si}}-O+\underset{\underset{R^2}{|}}{\overset{\overset{R^1}{|}}{Si}}-O\underset{x}{\Big]}\underset{\underset{R^2}{|}}{\overset{\overset{R^1}{|}}{Si}}+CH_2\underset{m}{)}\overset{O}{\overset{\|}{C}}-OR^3$$

wherein:

R¹ and R² are independently selected from methyl, ethyl and phenyl;

R⁴ is selected from methyl, ethyl, phenyl and a group represented by the formula:

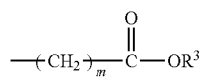

R³ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)₅CH3<br>\|<br>H5C2—C---CH2OH<br>\|<br>CH2OOC(CH2)₅CH3 | CH2OOC(CH2)₅CH3<br>\|<br>H5C2—C—CH2----<br>\|<br>CH2OOC(CH2)₅CH3 | where in this case the two esterified groups on the molecule have been reacted with heptanoic acid;

m is an integer from 5 to 22; and x is an integer from about 0 to about 1000.

In a preferred embodiment of the above silicone fluids, R¹ and R² are both methyl groups, m is from 10 to 14 and, more preferably, m is 10, x is from about 6 to about 110 and, more preferably, x is from about 6 to about 50.

Typically, R³ is a mono-hydroxy-terminated partially esterified ester residue which is derived from a mono-hydroxy-terminated partially esterified alcohol.

The mono-hydroxy-terminated partially esterified alcohol is preferably derived from di-, tri- or tetra-functional alcohol represented by the formula:

wherein:

R⁵ is an n-functional hydrocarbon residue; and n is from 2 to 8, preferably from 2 to 4.

Preferably, the di-, tri- or tetra-functional alcohol is ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, or a mixture thereof. Preferably, the di, tri- or tetra-functional alcohol is trimethylolpropane.

The R⁴ group can be either a methyl group or it can be a group represented by the formula:

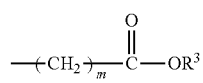

wherein R³ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)₅CH3<br>\|<br>H5C2—C---CH2OH<br>\|<br>CH2OOC(CH2)₅CH3 | CH2OOC(CH2)₅CH3<br>\|<br>H5C2—C—CH2----<br>\|<br>CH2OOC(CH2)₅CH3 | where in this case the two esterified groups on the molecule have been reacted with heptanoic acid;

m is an integer from 5 to 22; and x is an integer from about 0 to about 1000.

In a more preferred embodiment, the silicone ester compound is represented by the formula:

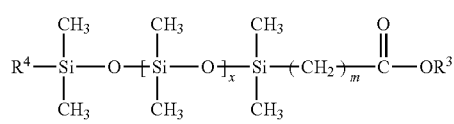

wherein:

R⁴ is a methyl or a group represented by the formula:

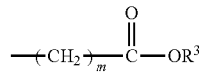

R³ is derived from a partially esterified ester residue, e.g., for a partially esterified trimetholpropane shown here, the residue is the structure without the remaining free hydroxyl group

| Partial Ester | Residue |
|---|---|
|  CH2OOC(CH2)5CH3<br>H5C2—C---CH2OH<br>CH2OOC(CH2)5CH3 | CH2OOC(CH2)5CH3<br>H5C2—C—CH2----<br>CH2OOC(CH2)5CH3 | where in this case the two esterified groups on the molecule have been reacted with heptanoic acid;

m is 10; and x is from about 6 to about 110.

More preferably, x is from about 6 to about 50, $R^3$ is a mono-hydroxy-terminated partially esterified ester residue derived from a mono-hydroxy-terminated partially esterified alcohol which, in turn, is derived from di-, tri- or tetra-functional alcohol represented by the formula:

$$R^5(OH)_n$$

wherein:

$R^5$ is an n-functional hydrocarbon residue; and n is an integer from 2 to 8, preferably from 2 to 4.

Examples of the di-, tri- or tetra-functional alcohols include ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

Trimethylolpropane is preferred.

The mono-hydroxy-terminated partially esterified ester can be represented by the formula:

$$(R^7COO)_{n-1}R^6(OH)$$

wherein:

$R^6$ is an (n-1)-functional hydrocarb residue group;

$R^7$ is a hydrocarbyl group; and n is an integer from 2 to 8, preferably from 2 to 4.

The present disclosure further provides a process for preparing a silicone ester compound including the step of contacting:

(i) a hydride terminated polysiloxane represented by the formula:

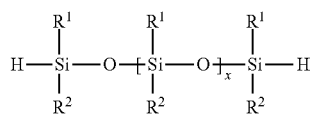

and (ii) a vinyl-terminated carboxylic acid ester of partially esterified ester represented by the formula:

$$CH_2{=}CH{-}(CH_2)_{m\text{-}2}{-}COOR^3$$

at a temperature and for a period of time sufficient to produce a silicone ester compound represented by the formula:

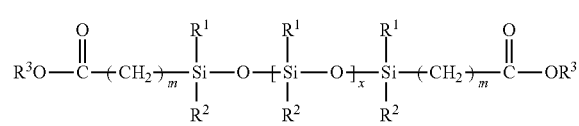

wherein:

$R^1$ and $R^2$ are independently selected from methyl, ethyl and phenyl;

$R^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)5CH3<br>H5C2—C---CH2OH<br>CH2OOC(CH2)5CH3 | CH2OOC(CH2)5CH3<br>H5C2—C—CH2----<br>CH2OOC(CH2)5CH3 | where in this case the two esterified groups on the molecule have been reacted with heptanoic acid;

m is an integer from 5 to 22; and x is an integer from about 0 to about 1000.

In a preferred embodiment of the process described above, $R^1$ and $R^2$ are both methyl groups, m is from 10 to 14, more preferably m is 10, x is from about 6 to about 110, and more preferably, x is from about 6 to about 50.

Preferably, $R^3$ is derived from a partially esterified ester residue, e.g., for a partially esterified trimetholpropane shown here, the residue is the structure without the remaining free hydroxyl group

| Partial Ester | Residue |
|---|---|
| CH2OOC(CH2)5CH3<br>H5C2—C---CH2OH<br>CH2OOC(CH2)5CH3 | CH2OOC(CH2)5CH3<br>H5C2—C—CH2----<br>CH2OOC(CH2)5CH3 | where in this case the two esterified groups on the molecule have been reacted with an acid, derived from a mono-hydroxy-terminated partially esterified alcohol derived from di-, tri- or tetra-functional alcohol represented by the formula:

$$R^5(OH)_n$$

wherein:

$R^5$ is an n-functional hydrocarbon residue; and n is an integer from 2 to 8, preferably from 2 to 4.

The di-, tri- or tetra-functional alcohol can be ethylene glycol, propylene glycol, butylene glycol, polyethylene glycol, neopentyl glycol polypropylene glycol, glycerin, trimethylolethane, trimethylolpropane, pentaerythritol, di-pentaerythritol, tri-pentaerythritol, or a mixture thereof.

Trimethylolpropane is preferred.

The mono-hydroxy-terminated partially esterified ester is represented by the formula:

$$(R^7COO)_{n-1}R^6(OH)$$

wherein:

$R^6$ is an (n-1)-functional hydrocarbon residue group;

$R^7$ is a hydrocarbyl group; and n is from 2 to 8, preferably from 2 to 4.

The vinyl-terminated carboxylic acid ester of partially esterified ester can be represented by the formula:

$$CH_2{=}CH{-}(CH_2)_{m\text{-}2}{-}COOR^6(OOCR^7)_{n-1}$$

wherein:

R⁶ is an (n-1)-functional hydrocarbon residue group;
R⁷ is a hydrocarbyl group;
m is an integer 5 to 22; and
n is an integer from 2 to 8, preferably from 2 to 4.

It is possible to have a much more complex structure at one or more positions of the silicone fluid. For example, the ester intermediate can have more than one free hydroxyl groups present. In this case, cross-linking via the ester groups is possible. Thus, each free hydroxyl group could react with the olefinic acid and the resulting product could then react with two silicone compounds.

The process for preparing a silicone fluid according to the present disclosure includes the step of contacting the hydride terminated polysiloxane and the vinyl-terminated carboxylic acid ester of partially esterified ester described herein. The hydride terminated polysiloxane and vinyl terminated carboxylic ester of a partially esterified ester are heated to 80-120° C. and a platinum hydrosilation catalyst such as chloroplatinic acid or any other platinum catalyst familiar to those skilled in the art is added at 5 to 100 ppm. Optionally, a solvent such as toluene, xylene, IPA or any other solvent that is familiar to those skilled in the art can be used. The reaction is heated at 80-120° C. until all silicone hydride is consumed, which usually takes about 2-8 hours. If a solvent is used, it is then stripped under vacuum.

The silicone ester compound according to the present disclosure has improved thermal oxidative stability as shown in the Pressure Differential Scanning Calorimetry (PDSC) Spectra measured in accordance with ASTM E2009-02.

Referring to FIG. 1, the Pressure Differential Scanning Calorimetry (PDSC) Spectrum of a fully esterified ester of trimethylol propane with linear octanoic and decanoic acids is seen.

Figure 2:
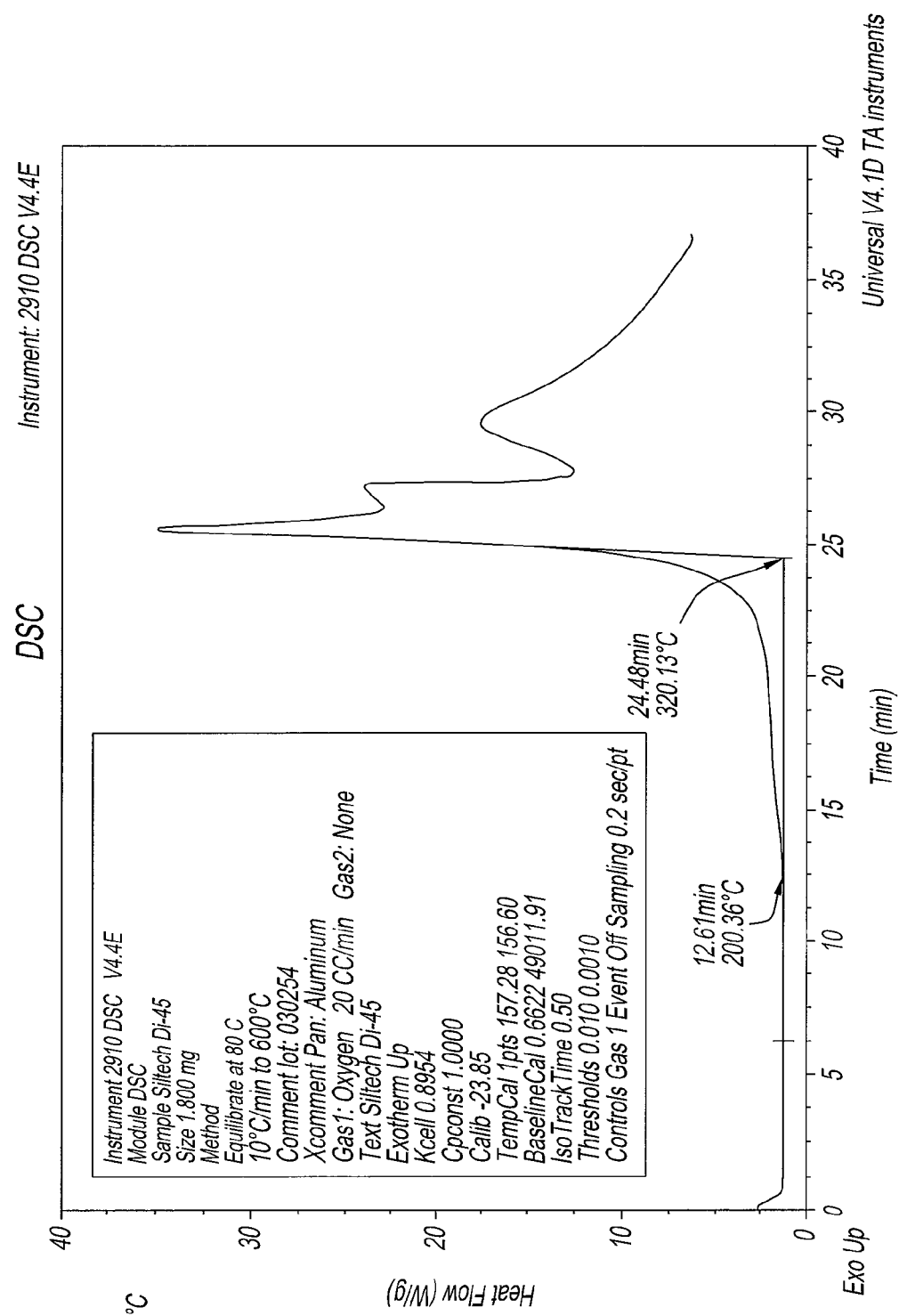
FIG. 2 shows the Pressure Differential Scanning Calorimetry (PDSC) Spectrum of a silicone based material SiOx where x is about 45.

FIG. 2 shows the Pressure Differential Scanning Calorimetry (PDSC) Spectrum of a silicone based material {Si—O}x where x is about 45.

Figure 3:
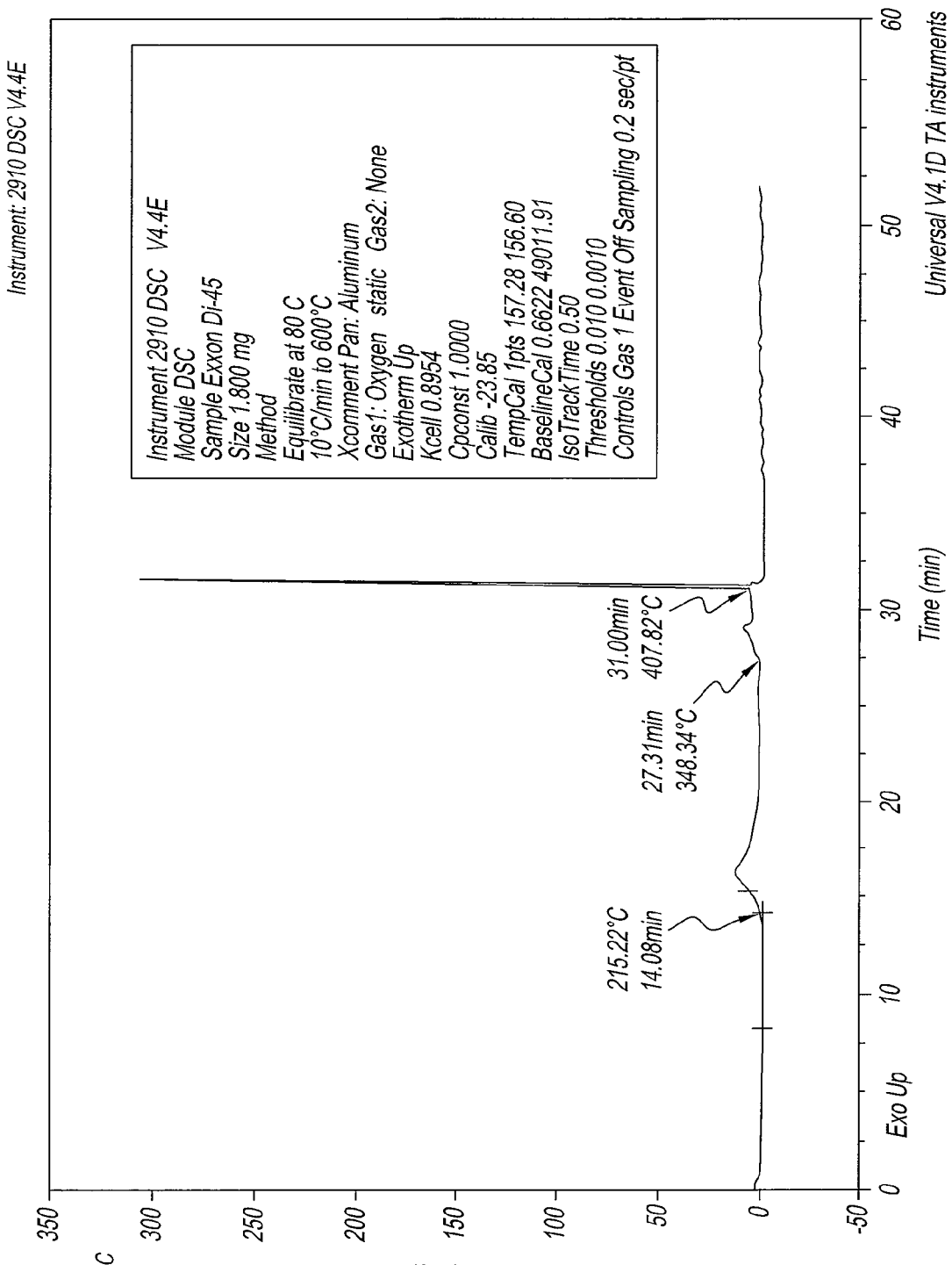
FIG. 3 shows the Pressure Differential Scanning Calorimetry (PDSC) Spectrum of a partial ester (OH#~135) reacted with undecylenic acid and a silicone based material SiOx where x is about 45.

FIG. 3 shows the Pressure Differential Scanning Calorimetry (PDSC) Spectrum of a partial ester (OH#~135) reacted with undecylenic acid and a silicone based material {Si—O}x where x is about 45.

Figure 4:
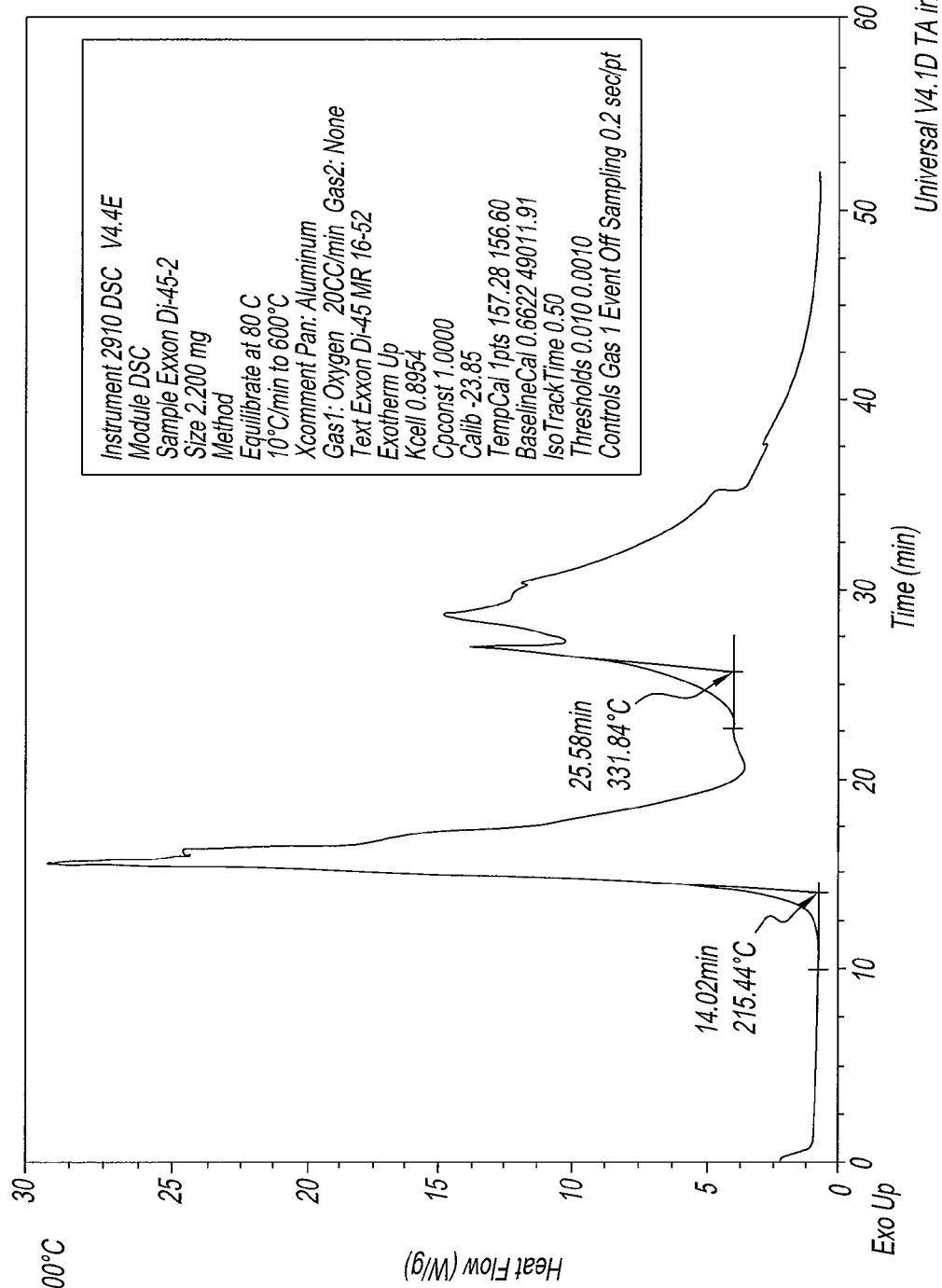
FIG. 4 shows the Pressure Differential Scanning Calorimetry (PDSC) Spectrum of a partial ester (OH#~80) reacted with undecylenic acid and silicone based material SiOx where x is about 45.

FIG. 4 shows the Pressure Differential Scanning Calorimetry (PDSC) Spectrum of a partial ester (OH#~80) reacted with undecylenic acid and silicone based material {Si—O}x where x is about 45.

Pressure Differential Scanning Calorimeter, PDSC, was used to generate the data in FIGS. 1-4. This test method, which is based on ASTM E2009-02, can be used to determine the oxidation properties of a material in the PDSC by linearly ramping the temperature in an oxygen rich environment. The instrument and the operating conditions used were:

| Instrument | TA 2910 DSC V4.4E |
|---|---|
| Sample size | 1–2 mg |
| Sample pan | Aluminum |
| Atmosphere | Oxygen |
| Pressure | 500 psi |
| Flow | 20 ml/min |
| Temperature | Equilibrate at 80° C. |
| | Ramp 10° C./min to 400° C. |

The Oxidative Onset Temperature, OOT, is determined during this test and represents the temperature at the point of intersection of the tangent drawn at the point of greatest slope on the heat flow versus temperature curve with the extrapolated baseline prior to the change in heat flow. Higher OOTs represent greater thermal oxidative stability among materials in a given test set.

In both cases, the functionalized esters have higher induction times and temperatures than the parent silicone and the fully esterified ester. In fact, the Pressure Differential Scanning Calorimetry (PDSC) Spectrum in FIG. 3 indicates that crosslinking of the functionalized silicones has occurred to produce a more thermal oxidatively stable molecule.

The results are summarized in the following table:

| Material | Oxidation | Onset Temperatures (° C.) |
|---|---|---|
| Fully Esterified Ester | 222 | |
| Silicone Starting Fluid | 320 | |
| Functional Material (FIG. 3) | 348 | 408* |
| Functional Material (FIG. 4) | 332 | |

*The second peak was noted on the material made with the fluid that initially had the higher partial ester concentration. Upon completion of the esterification step, more molecules are present with more than one vinyl bond which increases opportunities for cross-linking or chain propagation.

In FIGS. 3 and 4, a portion of each fluid has OOTs of ~215° C. This corresponds to trimethylolpropane that is fully esterified with a linear octanoic/decanoic acid blend (where hexanoic acid may be present up to 6 wt %, octanoic acid is generally present from 53 to 60 wt %, decanoic acid is generally present from 34 to 42 wt %, dodecanoic acid may be present up to 2 wt %). This fully esterified ester was produced during the reaction which also produced partially esterified ester. The partial ester was reacted with undecylenic acid and, subsequently, was reacted with the silicone based material. The fully esterified trimethylolpropane with a linear octanoic/decanoic acid blend was not removed from either of these reaction steps and was present in the final product. This fluid will hence forth be referred to as "free ester."

In addition, the functionalized esters shown have the following advantages:

(a) solubility in esters and, based on solubility parameters, in polyalphaolefins (PAOs) and mineral oils;

(b) colorless, clear, and odorless; and (c) high viscosity indices.

A functionalized ester was prepared by hydrosilating (1) an ester of undecylenic acid reacted with a partial ester of trimethylolpropane with a linear octanoic/decanoic acid blend with a (2) with a hydride terminated polysiloxane represented by the following formula

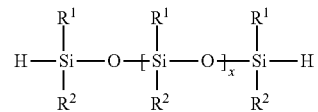

wherein:

$R^1$ and $R^2$ are methyl groups and x is approximately 45. The fluid viscosities and viscosity index (VI) of the product and of the functionalized esters are compared to the values that would be observed for the free ester and the hydride terminated polysiloxane in the following table:

Material

|  | C8/10 based Trimethylolpropane ester | functionalized Di-45 w/Ester | functionalized Di-45 ester {3} | Silicone Di-45 |
|---|---|---|---|---|
| Free Ester content, % | 100 | 18.8 | 0 | 0 |
| Kinematic Vis, cSt {1} & {2} |  |  |  |  |
| 40° C. | 19 | 186 | 315.6 | 38.3 |
| 100° C. | 4.3 | 51 | 90.5 | 16.3 |
| VI | 136 | 323 | 351 | 437 |

{1} ASTM method for kinematic vis is D445
{2} ASTM method for VI is D2270
{3} The results for the pure fractions were calculated using this logarithmic blending rule:
Ln (Blend Viscosity) = x1 * ln (viscosity1) + x2 * ln (viscosity2)
where
x = weight fraction of each component
viscosity = kinematic viscosity of each component In this equation, the viscosity of the blend {labeled functionalized Di-45 with ester can be measured directly. The properties of the free ester can be measured on a fully esterified product which would be produced separately. The weight fraction of the free ester can be determined by either gas chromatography or thermal gravimetric analyses (TGA) and the amount of functionalized ester can be determined by difference. As a result, all values in the equation are known except viscosity 2 (the viscosity of the functionalized ester) which can then be determined by direct substitution.

Another advantage for the silicone derivatized ester compounds is the very high viscosity index (ASTM D2270). The viscosities for the pure derivatives (no fully esterified ester present) have been back calculated and compared to other fluids (with similar 100 C Kinematic viscosities) in the following tables. For lube applications, these high VI fluids can help to provide formulations with better fuel economy and superior low temperature performance.

Improved VI with Much Better Oxidative Stability in all Three Cases

|  | Silicon Ester Exxon Di-10 | SpectraSyn 40 | Esterex C4461 |
|---|---|---|---|
| KV 100° C., cSt | 38 | 40 | 42.4 |
| Viscosity Index | 246 | 151 | 149 |
| OOT, ° C. | 347 | ~210 | ~215 | where functionalized Di-10 ester is
(1) ester of undecylenic acid reacted with a partial ester of trimethylolpropane with a linear octanoic/decanoic acid blend reacted
(2) with a hydride terminated polysiloxane represented by the following formula

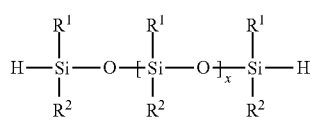

wherein:
$R^1$ and $R^2$ are methyl groups and x is approximately 10,
SpectraSyn 40 is a commercially available polyalphaolefin, and
Esterex C4461 was a commercially available complex ester.

|  | Silicon Ester Exxon Di-45 | SpectraSyn 100 |
|---|---|---|
| KV 100° C., cSt | 90.5 | 100 |
| Viscosity Index | 351 | 169 |
| OOT, ° C. | 344 | ~210 | where functionalized Di-45 ester is
(1) ester of undecylenic acid reacted with a partial ester of trimethylolpropane with a linear octanoic/decanoic acid blend reacted
(2) with a hydride terminated polysiloxane represented by the following formula

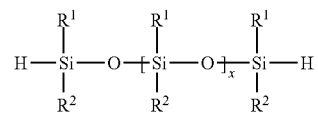

wherein:
$R^1$ and $R^2$ are methyl groups and x is approximately 45 and SpectraSyn 100 is a commercially available polyalphaolefin.

|  | Silicon Ester Exxon Di-100 | SpectraSyn Ultra 150 |
|---|---|---|
| KV 100° C., cSt | 178 | 150 |
| Viscosity Index | 415 | 214 |
| OOT, ° C. | 331 | ~210 | where functionalized Di-100 ester is
(1) ester of undecylenic acid reacted with a partial ester of trimethylolpropane with a linear octanoic/decanoic acid blend reacted
(2) with a hydride terminated polysiloxane represented by the following formula

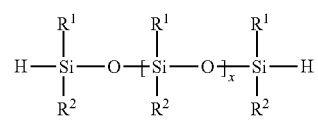

wherein:

$R^1$ and $R^2$ are methyl groups and x is approximately 100 and SpectraSyn 150 is a commercially available polyalphaolefin.

The product has outstanding oxidation characteristics as measured by ASTM D2272 in the Rotating Pressure Vessel. In this test, the fluid sample is placed in a glass-lined vessel along with water and a copper coil. The latter serves as an oxidation catalyst. The vessel is charged with oxygen to 90 psig and is placed in a constant temperature bath set at 150° C. The vessel is rotated axially at 100 rpm at a 30 degree angle from the horizontal. The time in minutes required for the pressure to drop to 25.4 psig is recorded. This interval is directly related to oxidative stability.

An example is a sample of the Exxon Di-100 (# MR18-82) which is a case where the silicone ester compound is represented by the formula:

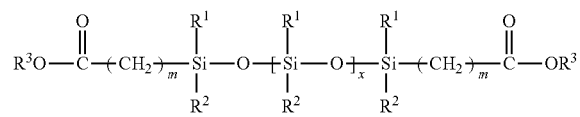

wherein x=~98, m=10, $R^1$ & $R^2$ are methyl groups, and $R^3$ is a linear $C_8$ to $C_{10}$ acid esterified with trimethylolpropane (TMP) so that there was substantially only one free hydroxyl group remaining before reaction with the undecylenic acid.

Data were collected on the fully esterified C8 to C10 acid TMP ester and the molecule pictured above in admixture with varying amounts of the fully esterified ester (as shown in the following table):

| Min* | wt % ester |
| --- | --- |
| 95 | 100 |
| 197.5 | 12.89 |
| 315 | 2.5 |

*The number of minutes required to reach a specific drop in gage pressure is the oxidation stability of the test sample, i.e., minutes required to achieve target drop in pressure.

Figure 5:
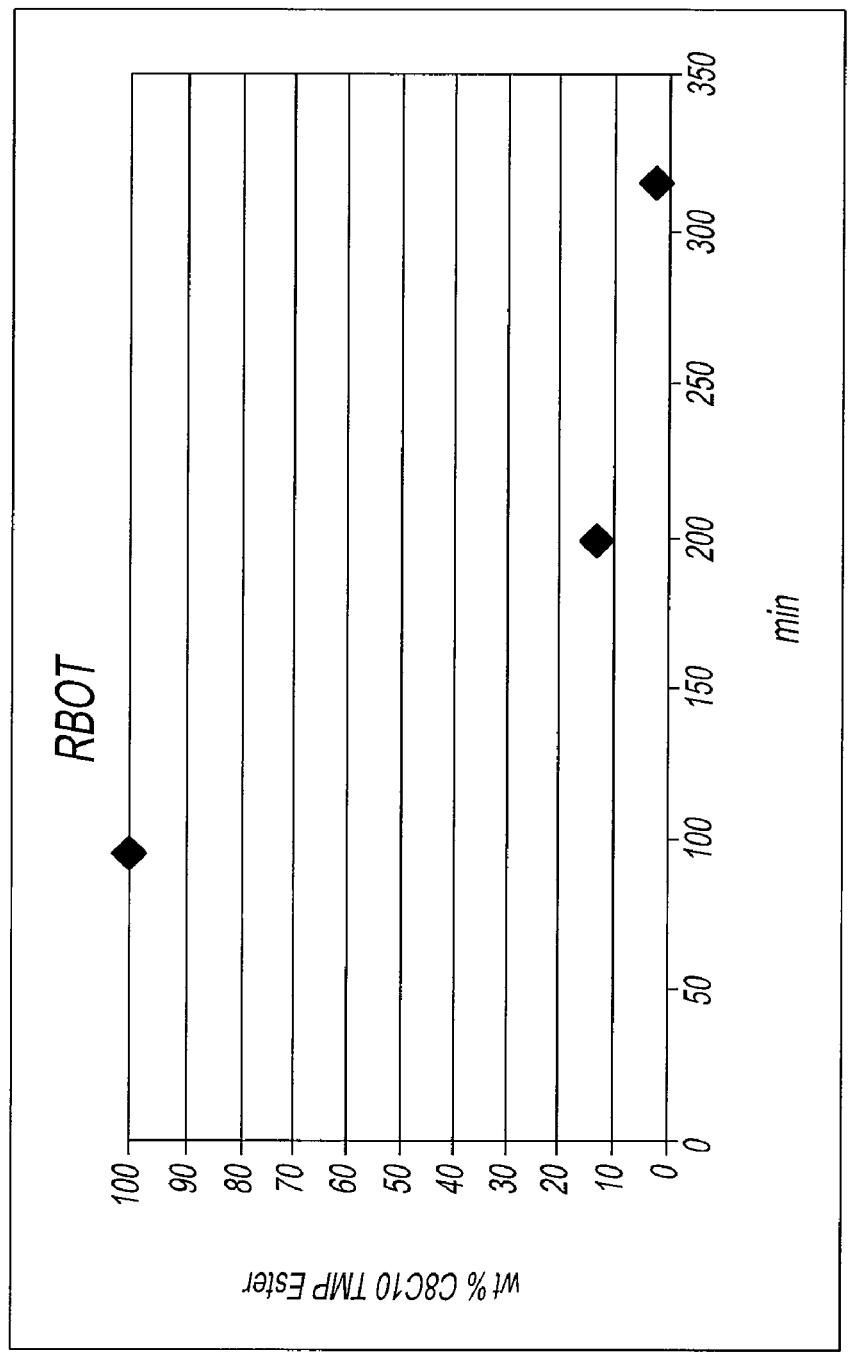
FIG. 5 is plot of wt % of the ester of trimethylolpropane with $C_8$ to $C_{10}$ acid versus oxidation induction time as measured by the rotating bomb oxidation test (RBOT), wherein $C_8$ to $C_{10}$ acid typically comprises a mixture of up to about 6 wt. % $C_6$, 53-60 wt. % $C_8$, 34-42 wt. % $C_{10}$, and up to about 2 wt. % $C_{12}$.

FIG. 5 is a plot of wt % of the free ester of trimethylolpropane reacted with $C_8$ to $C_{10}$ acid versus the time required to achieve the target pressure drop from the above table. The graph illustrates how the time increases as the "free" ester content of the mixture decreases.

Extrapolating to the pure derivatized fluid, the oxidative stability would be on the order of 350 minutes. Oxidative stability is very important in a number of applications (e.g. lubes, dielectric fluids, heat transfer fluids).

Another advantage for these silicone derivatized esters hinges on solubilities. The product from the final reactions which includes the free ester and the silicone derivatized ester were single phase fluids. There was no sign of incompatibility which can be observed when polyol esters are blended with silicones. The free ester in the products that were examined ranged from ~18 to 60 wt %.

Further tests were conducted with selected silicone derivatized esters that were separated from the bulk of the free ester by extraction with methanol. The amount of free ester was <2 wt % after the extraction. The products tested include the previously described Di-10, Di-45, and Di-100 and D2 and D10 which are described below:

D2 and D10 are silicone ester compounds that can be represented by the formula:

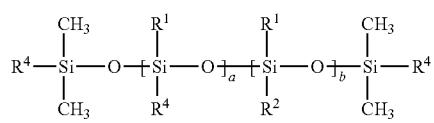

wherein $R^1$ and $R^4$ are methyl groups:

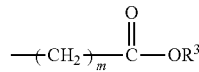

a is eight for D2 and 40 for D10;
b is four for D2 and D10;
m is 10; and
$R^2$ is derived from a hydroxy-terminated partially esterified ester of trimethylolpropane with a linear octanoic/decanoic acid blend These silicone derivatized esters were blended with various fluids to examine their solubilities. Mixtures of 10 wt % and 90 wt % of the derivatized ester and a test fluid were placed in a bottle at room temperature and shaken. Each bottle was subsequently examined to see if there was any indication that the silicon derivatized ester was not miscible in the test fluid. The results are summarized in the following table.

| | | Test Fluid, 90 wt % 10 wt % of | | | | |
| --- | --- | --- | --- | --- | --- | --- |
| | wt % Ester | SpectraSyn 4 | SpectraSyn 40 | Gr II EHC 45 | Dow 200 - 5 cSt | Dow 200 - 200 cSt |
| C8C10 TMP | 100 | S | S | S | H | H |
| Exxon Di-10 | <2 | S | vsl H | S | S | H |
| Exxon Di-45 | <2 | S | S | S | S | H |
| Exxon Di-100 | <2 | vsl H | H | S | S | vsl H |
| Exxon D2 | <2 | S | S | S | I | H |
| Exxon D10 | <2 | S | S | S | S | H |

SpectraSyn 4 and 40 are commercially available polyalphaolefins
EHC45 is a commercially available Group II Mineral Oil
Dow Corning 200 - 5 and 200 cSt are commercially available silicone fluids
vsl—very slightly
I—Insoluble
S—Soluble
H—Hazy The silicone derivatized ester compound can be tailored (e.g., changing the length of the silicone molecule, changing the point of attachment of the ester to the silicone molecule, changing the acids, anhydrides or alcohols used in creating the ester residue) to meet a variety of applications (e.g. additives or basestocks in lubes or emollients in personal care industry).

The present disclosure has been described with particular reference to the preferred embodiments. It should be understood that the foregoing descriptions and examples are only illustrative of the invention. Various alternatives and modifications thereof can be devised by those skilled in the art without departing from the spirit and scope of the present disclosure. Accordingly, the present disclosure is intended to embrace all such alternatives, modifications, and variations that fall within the scope of the appended claims.

What is claimed is:

1. A silicone composition having the formula:

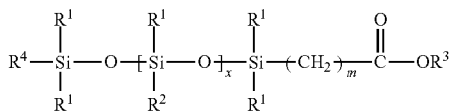

wherein:
$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

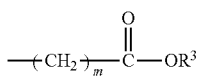

and a reverse ester thereof represented by the formula:

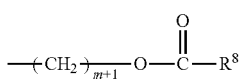

and the formula:

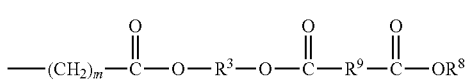

and a reverse ester thereof represented by the formula:

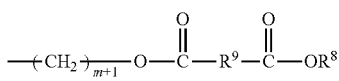

provided that if $R^1$ is anything but methyl or ethyl, then $R^2$ must be a methyl, ethyl or butyl,
$R^3$ is derived from a partially esterified ester residue;
$R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue;
$R^9$ is selected from the group consisting of: an arylene, an alkylene of 1 to 22 carbon atoms, substituted alkylene of 1 to 22 carbon atoms optionally substituted by one or more fluorine atoms and arylene;
$R^4$ is selected from the group consisting of: alkyl of 1 to 45 carbon atoms, substituted alkyl of 1 to 45 carbon atoms optionally substituted by one or more fluorine atoms, aryl, said ester-containing group and said compound derived from reverse esters thereof;
m is an integer between about 5 to about 22; and
x is an integer between about 0 to about 1000;
wherein said composition has at least 1 compound derived from said partially esterified ester-containing group or said reverse ester thereof.

2. The silicone composition of claim 1, wherein $R^1$ and $R^2$ are both methyl groups.

3. The silicone composition of claim 1, wherein m is an integer between about 10 to about 14.

4. The silicone composition of claim 3, wherein m is 10.

5. The silicone composition of claim 1, wherein x is an integer in the range between about 6 to about 110.

6. The silicone composition of claim 1, wherein x is an integer in the range between about 6 to about 50.

7. The silicone composition of claim 1, wherein said compound derived from said partially esterified ester residue is a partially esterified alcohol.

8. The silicone composition of claim 7, wherein said mono-hydroxy-terminated partially esterified alcohol is derived from di-, tri- or tetra-functional alcohol represented by the formula:

$$R^5(OH)_n$$

wherein:
$R^5$ is an n-functional hydrocarbon; and
n is from about 2 to about 8.

9. The silicone composition of claim 8, wherein said n is an integer in the range between about 2 to about 4.

10. The silicone composition of claim 8, wherein said functional alcohol is selected from the group consisting of: ethylene glycol, propylene glycol, butylene glycol, polyethylene glycol, neopentyl glycol, polypropylene glycol, glycerin, trimethylolethane, trimethylolpropane, pentaerythritol, di-pentaerythritol, tri-pentaerythritol, and a mixture thereof.

11. The silicone composition of claim 10, wherein said functional alcohol is trimethylolpropane.

12. The silicone composition of claim 1, wherein said compound derived from said partially esterified ester residue is a partially esterified acid.

13. The silicone composition of claim 12, wherein said mono-hydroxy-terminated partially esterified acid is derived from di-, tri- or tetra-functional acids.

14. The silicone composition of claim 13, wherein said functional acid is selected from the group consisting of: adipic acid, azelaic acid, sebacic acid, dodecanedioc acid, succinic acid, glutaric acid, maleic acid, phthalic acid, trimellitic acid, nadic acid, methyl nadic acid, hexahydrophthalic acid and mixtures thereof.

15. The silicone composition of claim 1, wherein $R^4$ is methyl group.

16. The silicone composition of claim 1, wherein $R^4$ is a group represented by the formula:

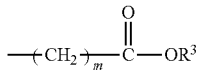

wherein:
R³ is a compound derived from a partially esterified ester residue;
m is an integer in the range between about 5 to about 22; and
x is an integer in the range between about 0 to about 1000, or a reverse ester thereof represented by the formula:

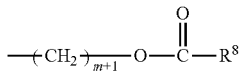

17. The silicone composition of claim 1, represented by the formula:

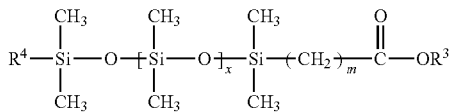

wherein:
$R^4$ is selected from the group consisting of methyl and a group represented by the formula:

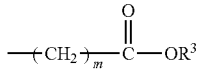

R³ is a compound derived from a partial ester residue;
m is 10; and
x is an integer in the range between about 0 to about 1000.

18. The silicone composition of claim 17, wherein x is from about 6 to about 110.

19. The silicone composition of claim 17, wherein $R^4$ is a group represented by the formula:

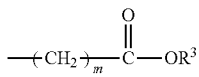

wherein R³ is a compound derived from a partially esterified ester residue.

20. The silicone composition of claim 19, wherein said partially esterified ester residue is derived from a mono-hydroxy-terminated partially esterified alcohol.

21. The silicone composition of claim 20, wherein said mono-hydroxy-terminated partially esterified alcohol is derived from di-, tri- or tetra-functional alcohol represented by the formula:

wherein:
$R^5$ is an n-functional hydrocarbon residue; and
n is an integer in the range between about 2 to about 8.

22. The silicon composition of claim 20, wherein n is between about 2 to about 4.

23. The silicone composition of claim 21, wherein said di-, tri- or tetra-functional alcohol is selected from the group consisting of: ethylene glycol, propylene glycol, butylene glycol, polyethylene glycol, neopentyl glycol polypropylene glycol, glycerin, trimethylolethane, trimethylolpropane, pentaerythritol, di-pentaerythritol, tri-pentaerythritol, and a mixture thereof.

24. The silicone composition of claim 23, wherein said functional alcohol is trimethylolpropane.

25. The silicone composition of claim 17, wherein $R^4$ is methyl group.

26. The silicone composition of claim 20, wherein said partially esterified ester is represented by the formula:

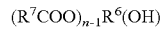

wherein:
$R^6$ is an (n-1)-functional hydrocarbon residue group;
$R^7$ is a hydrocarbyl group; and
n is an integer in the range between about 2 to about 8.

27. A silicone composition represented by the formula:

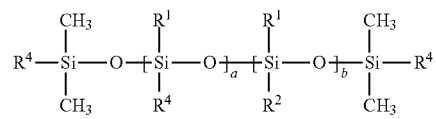

wherein
$R^1$ are independently selected from the group consisting of: an alkyl having 1-5 carbon atoms, a substituted alkyl having 1-5 carbon atoms optionally substituted by one or more fluorine atoms, and a phenyl, and $R^2$ is selected from the group consisting of: hydrogen, alkyl of 1 to 45 carbon atoms, substituted alkyl of 1 to 45 carbon atoms optionally substituted by one or more fluorine atoms, aryl, a partially esterified ester-containing group represented by the formula:

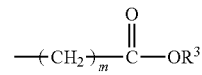

and a reverse ester thereof represented by the formula:

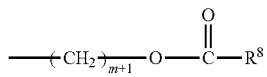

and the formula:

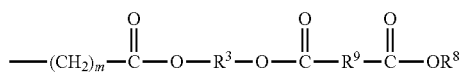

and a reverse ester thereof represented by the formula:

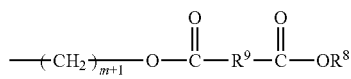

provided that if $R^1$ is anything but methyl or ethyl, then $R^2$ must be a methyl, ethyl or butyl, $R^4$ is selected from the group consisting of: alkyl and a group represented by the formula:

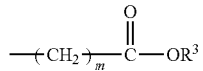

wherein:

a is an integer in the range between about 1 to about 20;

b is an integer in the range between about 0 to about 1000;

$R^3$ is a compound derived from a partially esterified ester residue; $R^8$ is selected from the group consisting of: hydrogen, alkyl of 1 to 45 carbon atoms, substituted alkyl of 1 to 45 carbon atoms optionally substituted by one or more fluorine atoms, aryl and a compound derived from a partially esterified ester residue; $R^9$ is selected from the group consisting of: an arylene, an alkylene of 1 to 22 carbon atoms, substituted alkylene of 1 to 22 carbon atoms optionally substituted by one or more fluorine atoms and arylene; and m is an integer in the range between about 5 to about 22; with the proviso that the $R^4$ groups are not all alkyls.

* * * * *